United States Patent [19]

Desai et al.

[11] Patent Number: 5,994,286

[45] Date of Patent: Nov. 30, 1999

[54] ANTIBACTERIAL COMPOSITION CONTAINING TRICLOSAN AND TOCOPHEROL

[75] Inventors: Sureshchandra G. Desai, deceased, late of Wayne, by Bhanumati Desai, Administratrix; Arturo Valdes, North Bergen, both of N.J.

[73] Assignee: Henkel Corporation, Gulph Mills, Pa.

[21] Appl. No.: 08/898,546

[22] Filed: Jul. 22, 1997

[51] Int. Cl.$^6$ ............................. C11D 3/48; C11D 3/22; C11D 11/00

[52] U.S. Cl. ..................... 510/386; 510/131; 510/321; 510/470

[58] Field of Search ................... 510/470, 131, 510/321, 383, 386, 387, 388, 382; 252/FOR 239, FOR 131

[56] References Cited

U.S. PATENT DOCUMENTS

| | | | |
|---|---|---|---|
| 3,664,961 | 5/1972 | Norris | 252/99 |
| 4,224,319 | 9/1980 | Marcadet | 424/238 |
| 4,228,044 | 10/1980 | Cambre | 252/547 |
| 4,414,128 | 11/1983 | Goffinet | 252/111 |
| 4,758,370 | 7/1988 | Jungermann et al. | 252/132 |
| 5,266,690 | 11/1993 | McCurry, Jr. et al. | 536/18.6 |
| 5,332,528 | 7/1994 | Pan et al. | 252/548 |
| 5,364,031 | 11/1994 | Taniguchi et al. | 239/330 |
| 5,417,875 | 5/1995 | Nozaki | 252/106 |
| 5,449,763 | 9/1995 | Wulff et al. | 536/18.6 |
| 5,635,469 | 6/1997 | Fowler et al. | 510/406 |
| 5,646,100 | 7/1997 | Haugk et al. | 510/131 |
| 5,716,626 | 2/1998 | Sakurai et al. | 424/401 |
| 5,719,113 | 2/1998 | Fendler et al. | 510/382 |
| 5,734,029 | 3/1998 | Wulff et al. | 536/4.1 |

OTHER PUBLICATIONS

Hawley's Condensed Chemical Dictionary, 12th Ed. (1993), definitions of "preservative", "surface–active agent" & "tocopherol" (pp. 962, 1108 & 1156).

RD 21313 ("Control of discoloration of phenolic compounds, especially in soaps"), Jan. 1982.

*Primary Examiner*—Ardith Hertzog
*Attorney, Agent, or Firm*—Ernest G. Szoke; Wayne C. Jaeschke; Steven J. Trzaska

[57] ABSTRACT

An aqueous antimicrobial cleaning composition comprising: (a) a surfactant; (b) triclosan; and (c) a tocopherol and a process for inhibiting the color degradation of an aqueous antimicrobial cleaning composition involving the addition of an effective amount of a tocopherol thereto.

25 Claims, No Drawings

ANTIBACTERIAL COMPOSITION CONTAINING TRICLOSAN AND TOCOPHEROL

FIELD OF THE INVENTION

The present invention generally relates to an antimicrobial composition. More particularly, the invention relates to an antimicrobial composition having enhanced color stability when exposed to UV light.

BACKGROUND OF THE INVENTION

Industrial antimicrobial agents are chemical compositions that are used to prevent microbiological contamination and deterioration of commercial products, materials and systems. The following chemical classes of antimicrobial agents are recognized in industry applications: phenolics; halogen compounds, quaternary ammonium compounds; metal derivatives; amines; alkanolamines and nitro derivatives; anilides; and organo-sulfur and sulfur-nitrogen compounds.

A given antimicrobial agent may either destroy all of the microbes present or just prevent their further proliferation to numbers that would be significantly destructive to the substrate or system being protected. The terms, microbes and microorganisms, refer primarily to bacteria and fungi. Each of these groups is subdivided into two general subclasses: gram-positive and gram-negative bacteria, and among the fungi, molds and yeasts.

Areas of application for antimicrobial agents include cosmetics, disinfectants and sanitizers, wood preservatives, food and animal feeds, paint, cooling water, metalworking fluids, hospital and medical uses.

Of the numerous antimicrobial compounds which are available for use, the phenolic compound dihydric phenol 2,4,4'-trichloro-2'-hydroxydiphenyl ether (a.k.a. triclosan), is perceived as being the most desirable. This antimicrobial agent, however, when incorporated into surfactant compositions containing surfactants whether anionic, cationic, nonionic, amphoteric, zwitterionic, and the like, has a tendency to undergo color degradation when exposed to UV light (either sunlight or indoor light) over prolonged periods of time due to the oxidative formation of free radicals within the system. Thus, an antimicrobial hand soap composition containing triclosan as an antimicrobial agent will, over time, turn dark in color due to the penetration of UV rays through the container, causing it to appear dirty in color.

It is therefore an object of the present invention to enhance the color stability of surfactant compositions containing triclosan as an antimicrobial agent by inhibiting free radical formation.

SUMMARY OF THE INVENTION

The present invention is directed to an aqueous antimicrobial cleaning composition containing:

(a) a surfactant;
(b) triclosan; and
(c) a tocopherol.

The present invention is also directed to a process for making an aqueous antimicrobial cleaning composition having enhanced color stability upon exposure to ultraviolet light involving:

(a) providing a surfactant component;
(b) providing a triclosan component;
(c) providing a tocopherol component; and
(d) mixing components (a)–(c) to form an antimicrobial surfactant composition.

DESCRIPTION OF THE INVENTION

Other than in the operating examples, or where otherwise indicated, all numbers expressing quantities of ingredients or reaction conditions are understood as being modified in all instances by the term "about".

The surfactant composition of the present invention is generally comprised of water and at least one surfactant selected from the group consisting of anionics, nonionics, cationics, amphoterics and zwitterionics. A typical listing of the classes and species of these surfactants is given in U.S. Pat. No. 3,664,961, the entire contents of which is hereby incorporated by reference. These surfactants can be used individually or in combination at levels in the range of from about 8 to about 40% by weight, and preferably from about 30 to about 40% by weight, based on the total weight of the aqueous antimicrobial composition.

Suitable anionic surfactants include, but are not limited to, water-soluble salts of alkyl benzene sulfonates, alkyl sulfates, alkyl polyethoxy ether sulfates, paraffin sulfonates, alpha-olefin sulfonates and sulfosuccinates, alpha-sulfocarboxylates and their esters, alkyl glyceryl ether sulfonates, fatty acid monoglyceride sulfates and sulfonates, and alkyl phenol polyethoxyether sulfates.

Other suitable anionic surfactants include the water-soluble salts or esters of alpha-sulfonated fatty acids containing from about 6 to about 20 carbon atoms in the fatty acid group and from about 1 to about 10 carbon atoms in the ester group.

A particularly preferred anionic surfactant for use in the present invention is sodium lauryl sulfate.

Suitable nonionic surfactants which may be employed in the present invention include, but are not limited to, alkyl polyglycosides, polyethylene oxide condensates of alkyl phenol having an alkyl group containing from about 6 to about 12 carbon atoms in either straight or branched-chain configuration, the ethylene oxide being present in amounts equal to from 5 to 25 moles of ethylene oxide per mole of alkyl phenol.

Condensation products of primary or secondary alcohols having from 8 to 24 carbon atoms, with from 1 to about 30 moles of alkylene oxide per mole of alcohol may also be employed.

The alkyl polyglycosides which can be used as nonionic surfactants in the composition are generally represented by formula I:

$$R_1O(R_2O)_b(Z)_a \qquad \text{I}$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6. Preferred alkyl polyglycosides which can be used in the compositions according to the invention have the formula I wherein Z is a glucose residue and b is zero. Such alkyl polyglycosides are commercially available, for example, as APG®, GLUCOPON®, or PLANTAREN® surfactants from Henkel Corporation, Ambler, Pa., 19002. Examples of such surfactants include but are not limited to:

1. APG® 225 Surfactant—an alkyl polyglycoside in which the alkyl group contains 8 to 10 carbon atoms and having an average degree of polymerization of 1.7.

2. GLUCOPON® 425 Surfactant—an alkyl polyglycoside in which the alkyl group contains 8 to 16 carbon atoms and having an average degree of polymerization of 1.48.
3. GLUCOPON® 625 Surfactant—an alkyl polyglycoside in which the alkyl group contains 12 to 16 carbon atoms and having an average degree of polymerization of 1.6.
4. APG® 325 Surfactant—an alkyl polyglycoside in which the alkyl group contains 9 to 11 carbon atoms and having an average degree of polymerization of 1.5.
5. GLUCOPON® 600 Surfactant—an alkyl polyglycoside in which the alkyl group contains 12 to 16 carbon atoms and having an average degree of polymerization of 1.4.
6. PLANTAREN® 2000 Surfactant—an alkyl polyglycoside in which the alkyl group contains 8 to 16 carbon atoms and having an average degree of polymerization of 1.4.
7. PLANTAREN® 1300 Surfactant—an alkyl polyglycoside in which the alkyl group contains 12 to 16 carbon atoms and having an average degree of polymerization of 1.6.

Other examples include alkyl polyglycoside surfactant compositions which are comprised of mixtures of compounds of formula I wherein Z represents a moiety derived from a reducing saccharide containing 5 or 6 carbon atoms; a is a number having a value from 1 to about 6; b is zero; and $R_1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and polyglycosides, in the resulting product changes and the concentration in the product of the polyglycosides relative to the monoglycoside increases as well as the concentration of individual polyglycosides to the total, i.e., DP2 and DP3 fractions in relation to the sum of all DP fractions. Such compositions are disclosed in U.S. Pat. No. 5,266,690, the entire contents of which are incorporated herein by reference.

Other alkyl polyglycosides which can be used in the compositions according to the invention are those in which the alkyl moiety contains from 6 to 18 carbon atoms in which and the average carbon chain length of the composition is from about 9 to about 14 comprising a mixture of two or more of at least binary components of alkylpolyglycosides, wherein each binary component is present in the mixture in relation to its average carbon chain length in an amount effective to provide the surfactant composition with the average carbon chain length of about 9 to about 14 and wherein at least one, or both binary components, comprise a Flory distribution of polyglycosides derived from an acid-catalyzed reaction of an alcohol containing 6–20 carbon atoms and a suitable saccharide from which excess alcohol has been separated.

A particularly preferred nonionic surfactant for use in the present invention is an alkyl polyglycoside of formula I wherein $R_1$ is a monovalent organic radical having from about 12 to about 16 carbon atoms, b is zero, and a is a number having a value of from about 1.4 to about 1.8, and preferably about 1.6.

Suitable amphoteric surfactants include water-soluble derivatives of aliphatic secondary and tertiary amines in which the aliphatic moiety can be straight chain or branched and wherein one of the aliphatic substituents contains from about 8 to 18 carbon atoms and one contains an anionic water-solubilizing group, e.g., carboxy, sulfonate, sulfate, phosphate or phosphonate.

Suitable zwitterionic surfactants include water-soluble derivatives of aliphatic quaternary ammonium phosphonium and sulfonium cationic compounds in which the aliphatic moieties can be straight chain or branched, and wherein one of the aliphatic substituents contains from about 8 to 18 carbon atoms and one contains an anionic water-solubilizing group.

Suitable cationic surfactants include the ammonium surfactants such as alkyldimethyl ammonium halogenides, and those surfactants having the formula:

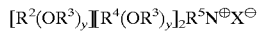

$$[R^2(OR^3)_y][R^4(OR^3)_y]_2R^5N^\oplus X^\ominus$$

wherein $R^2$ is an alkyl or alkyl benzyl group having from about 8 to about 18 carbon atoms in the alkyl chain, each $R^3$ is selected from the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl, ring structures formed by joining the two $R^4$ groups, —$CH_2CHOHCHOHCOR^6$ —$CHOHCH_2OH$ wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion. Cationic surfactants of this type are generally described in U.S. Pat. No. 5,332,528, the entire contents of which is incorporated herein by reference.

Other cationic surfactants useful herein are also described in U.S. Pat. No. 4,228,044, issued Oct. 14, 1980, incorporated herein by reference.

The antimicrobial agents employed in the present invention are generally halo-substituted dihydric phenol compounds and specifically, a dihydric phenol 2,4,4'-trichloro-2'-hydroxydiphenyl ether (a.k.a. triclosan).

Tocopherol compounds occur in many vegetable and animal oils and are also referred to as vitamin E. The vitamin E relates to the physiological effect of these food ingredients.

There are eight naturally occurring substances with vitamin E activity. They are derivatives of 6-chromanol and belong to two groups of compounds. The first group is derived from tocol and carries a saturated isoprenoidal side chain containing 16 carbon atoms. This group includes alpha-, beta-, gamma-, and delta-tocopherol. The compounds differ in their degree of methylation at the benzene ring of the tocol. Alpha-tocopherol is the substance with the strongest biological vitamin E effect and the greatest technical and economical importance. It is the dominant tocopherol in human and animal tissue.

The second group of substances with vitamin E activity are the derivatives of tocotrienol. They differ from the other tocopherol homologs in the unsaturated isoprenoidal side chain containing 16 carbon atoms. The naturally occurring tocoenols also show vitamin E activity and are normally isolated from their natural sources together with the saturated tocopherol homologs in the recovery of vitamin E. In the context of the present invention, the name "tocopherol" is also intended to encompass these tocopherol homologs, i.e. tocopherol are found in vegetable oils, such as wheatgerm oil, corn oil, soybean oil and palm kernel oil. However, tocopherol is also found in other vegetable oils, for example in safflower oil, peanut oil, cottonseed oil, sunflower oil, rapeseed oil, palm oil and other vegetable oils.

The natural plant oils contain only small quantities of tocopherol. Concentration is undesirable for commercial applications. In addition, impurities are supposed to be removed to enhance the antioxidizing effect and vitamin E activity. Accordingly, the most important natural sources of tocopherol are not the vegetable oils themselves, but rather the steam distillates—also known as steamer distillates—obtained in the deodorization of vegetable and animal oils. Although the tocopherols are obtained in concentrated form, they are mixed with sterol and sterol esters, free fatty acids and triglycerides. The distillate from the deodorization of soybean oil is particularly interesting. The soybean oil steamer distillate contains approximately 10% (maximum) by weight mixed tocopherols and the same amount of sterols which are predominantly present in their ester form.

Tocopherol concentrates are obtained from secondary products of the deodorization of oils and fats by esterification of the free fatty acids present therein by addition of an alcohol or by removal of the free fatty acids from the distillates by distillation, after which these products are subjected to hydrogenation and subsequently to solvent fractionation to extract the tocopherols. In a particularly preferred embodiment of the present invention, alpha-tocopherols are employed as the color stabilizing agents.

According to one embodiment of the present invention, there is provided an aqueous antimicrobial cleaning composition containing: (a) from about 8 to about 40% by weight, and preferably from about 30 to about 40% by weight of a surfactant selected from the group consisting of anionics, cationics, nonionics, amphoterics, zwitterionics and mixtures thereof; (b) from about 0.1 to about 3.0% by weight, and preferably from about 0.2 to about 1.0% by weight of triclosan; and (c) from about 0.1 to about 0.6% by weight, and preferably from about 0.1 to about 0.5% by weight of a tocopherol, all weights being based on the total weight of the composition.

It should be noted that various auxiliaries typically contained in cleaning compositions may also be added without departing from the spirit of the invention. Examples of suitable auxiliaries include, but are not limited to, hydrotropes, dyes, perfumes, enzymes, chlorine releasing agents, soil suspending agents, thickeners and foam modifiers.

According to another aspect of the present invention, there is also provided a process for making an aqueous antimicrobial cleaning composition having enhanced color stability upon exposure to ultraviolet light involving combining the above-disclosed components in the above-disclosed proportions. The components may be combined by any conventional manner such as, by stirring.

The components will generally be combined at a temperature ranging from about 60 to about 80° C., and preferably from about 65 to about 75° C., and a pH ranging from about 4 to about 8, and preferably from about 5.5 to about 7.5.

The present invention will be better understood from the examples which follow, all of which are meant to be illustrative only and are not meant to unduly limit the scope of the invention in any way.

EXAMPLES

Antibacterial compositions in accordance with the present invention were prepared and analyzed for color degradation.

Example 1

| Component | % wt./wt. |
|---|---|
| sodium lauryl sulfate (29% active) | 66.7 |
| lauryl glycoside (50% active) | 15.6 |
| cocamidopropyl betaine (31% active) | 11.7 |
| triclosan | 1.0 |
| glycerine | 1.0 |
| propyplene glycol | 1.0 |
| sodium chloride | 2.0 |
| tocopherol | 0.3 |
| water | QS to 100 |

Example 2

| Component | % wt./wt. |
|---|---|
| sodium lauryl sulfate (29% active) | 66.7 |
| lauryl glycoside (50% active) | 15.6 |
| cocamidopropyl betaine (31% active) | 11.7 |
| triclosan | 1.0 |
| glycerine | 1.0 |
| propyplene glycol | 1.0 |
| sodium chloride | 2.0 |
| tocopherol | 0.4 |
| water | QS to 100 |

Comparative Example 1

| Component | % wt./wt. |
|---|---|
| sodium lauryl sulfate (29% active) | 66.7 |
| lauryl glycoside (50% active) | 15.6 |
| cocamidopropyl betaine (31% active) | 11.7 |
| triclosan | 1.0 |
| glycerine | 1.0 |
| propyplene glycol | 1.0 |
| sodium chloride | 2.0 |
| water | QS to 100 |

Examples 1 and 2 were found to maintain their original color when exposed to room lighting, at room temperature, even after a period of 12 months. Comparative Example 1, under the same physical conditions, became dark amber in color within one month. Therefore, the results show that the presence of a tocopherol in an antibacterial composition inhibits its color degradation over prolonged periods of exposure to light.

What is claimed is:

1. An aqueous antimicrobial cleaning composition comprising:
    (a) from about 8 to about 40% by weight, based on the weight of the composition, of a surfactant;
    (b) triclosan; and
    (c) a discoloration inhibiting agent consisting of a tocopherol.

2. The composition of claim 1 wherein the surfactant is selected from the group consisting of anionics, cationics, nonionics, amphoterics, zwitterionics and mixtures thereof.

3. The composition of claim 2 wherein the surfactant is an alkyl polyglycoside of formula I:

$$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6.

4. The composition of claim 3 wherein in formula I, $R_1$ is a monovalent organic radical having from about 12 to about 16 carbon atoms, b is zero, and a is a number having a value of from about 1.4 to about 1.8.

5. The composition of claim 1 wherein the tocopherol is alpha-tocopherol.

6. The composition of claim 5 wherein the tocopherol is present in the composition in an amount of from about 0.1 to about 0.6% by weight, based on the weight of the composition.

7. The composition of claim 6 wherein the tocopherol is present in the composition in an amount of from about 0.1 to about 0.5% by weight, based on the weight of the composition.

8. The composition of claim 1 wherein the triclosan is present in the composition in an amount of from about 0.1 to about 3.0% by weight, based on the weight of the composition.

9. The composition of claim 8 wherein the triclosan is present in the composition in an amount of from about 0.2 to about 1.0% by weight, based on the weight of the composition.

10. The composition of claim 1 wherein the surfactant is present in the composition in an amount of from about 30 to about 40% by weight, based on the weight of the composition.

11. The composition of claim 1 further comprising an auxiliary selected from the group consisting of hydrotropes, dyes, perfumes, enzymes, chlorine releasing agents, soil suspending agents, thickeners, foam modifiers and mixtures thereof.

12. An aqueous antimicrobial cleaning composition comprising:
   (a) from about 30 to about 40% by weight of a surfactant selected from the group consisting of anionics, nonionics, cationics, amphoterics, zwitterionics and mixtures thereof;
   (b) from about 0.2 to about 1.0% by weight of triclosan;
   (c) from about 0.1 to about 0.5% by weight of, a discoloration inhibiting agent consisting of an alpha-tocopherol, all weights being based on the weight of the composition.

13. The composition of claim 12 wherein the surfactant is an alkyl polyglycoside of formula I:

$$R_1O(R_2O)_b(Z)_a \qquad I$$

wherein $R_1$ is a monovalent organic radical having from about 12 to about 16 carbon atoms; $R_2$ is a divalent alkylene radical having from 2 to 4 carbon atoms; Z is a saccharide residue having 5 or 6 carbon atoms; b is zero; a is a number having a value from about 1.4 to about 1.8.

14. A process for inhibiting color degradation of an aqueous antimicrobial cleaning composition, the process comprising: (a) providing an aqueous antimicrobial cleaning composition containing: (i) from about 8 to about 40% by weight of a surfactant component; and (ii) a triclosan component; and (b) adding an effective amount of, a discoloration inhibiting agent consisting of a tocopherol component to the composition.

15. The process of claim 14 wherein the surfactant is selected from the group consisting of anionics, cationics, nonionics, amphoterics, zwitterionics and mixtures thereof.

16. The process of claim 15 wherein the surfactant is an alkyl polyglycoside of formula I:

$$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6.

17. The process of claim 16 wherein in formula I, $R_1$ is a monovalent organic radical having from about 12 to about 16 carbon atoms, b is zero, and a is a number having a value of from about 1.4 to about 1.8.

18. The process of claim 14 wherein the triclosan is present in the composition in an amount of from about 0.1 to about 3.0% by weight, based on the weight of the composition.

19. The process of claim 18 wherein the triclosan is present in the composition in an amount of from about 0.2 to about 1.0% by weight, based on the weight of the composition.

20. The process of claim 14 wherein the tocopherol is present in the composition in an amount of from about 0.1 to about 0.6% by weight, based on the weight of the composition.

21. The process of claim 20 wherein the tocopherol is present in the composition in an amount of from about 0.1 to about 0.5% by weight, based on the weight of the composition.

22. The process of claim 14 wherein the surfactant is present in the composition in an amount of from about 30 to about 40% by weight, based on the weight of the composition.

23. The process of claim 14 wherein the tocopherol is alpha-tocopherol.

24. The process of claim 14 wherein the composition further comprises an auxiliary component selected from the group consisting of hydrotropes, dyes, perfumes, enzymes, chlorine releasing agents, soil suspending agents, thickeners, foam modifiers and mixtures thereof, to the composition.

25. A process for inhibiting the color degradation of an aqueous antimicrobial cleaning composition containing from about 8 to about 40% by weight of a surfactant component and a triclosan component, the process comprising adding from about 0.1 to about 0.5% by weight, based on the weight of the composition, a discoloration inhibiting agent consisting of of a tocapherol component, to the composition.

* * * * *